United States Patent [19]

Mantovanini et al.

[11] Patent Number: 5,436,262
[45] Date of Patent: Jul. 25, 1995

[54] PHARMACOLOGICALLY ACTIVE DERIVATIVES OF 2-(BENZIMIDAZOL-2-YL)-1,3-DIAMINO-PROPANE

[75] Inventors: Marco Mantovanini; Roberto Curti, both of Milan, Italy

[73] Assignee: Dompé Farmaceutici SpA, Milan, Italy

[21] Appl. No.: 243,627

[22] Filed: May 16, 1994

[30] Foreign Application Priority Data

May 14, 1993 [IT] Italy .................... MI93A0994

[51] Int. Cl.[6] ............. A61K 31/415; C07D 235/14; C07D 407/14; C07D 407/04

[52] U.S. Cl. .................... 514/394; 514/316; 514/322; 546/187; 546/199; 548/306.1; 548/309.7

[58] Field of Search ............ 514/316, 322, 394; 546/187, 199; 548/306.1, 309.7

[56] References Cited

FOREIGN PATENT DOCUMENTS 0350467 12/1993 European Pat. Off. .

*Primary Examiner*—Patricia L. Morris
*Attorney, Agent, or Firm*—Stevens, Davis, Miller & Mosher

[57] ABSTRACT

Derivatives of 2-(benzimidazol-2-yl)-1,3-diaminopropane, the process for their preparation as well as the pharmaceutical compositions containing them as active ingredients are described. The compounds exhibit antiallergic activity.

6 Claims, No Drawings

PHARMACOLOGICALLY ACTIVE DERIVATIVES OF 2-(BENZIMIDAZOL-2-YL)-1,3-DIAMINOPROPANE

Pharmacologically active derivatives of 2-(benzimidazol-2-yl)-1,3-diaminopropane and the process for their preparation are the object of the present invention. More particularly the derivatives of 2-(benzimidazol-2-yl)-1,3-diaminopropane belong to the class of compounds of the general formula

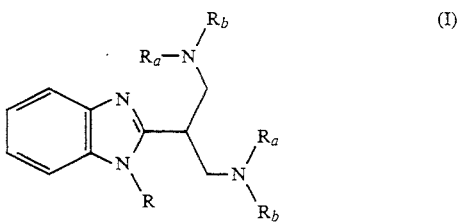

wherein
R is selected from the group consisting of ethoxyethyl, allyloxyethyl, benzyl, 4-fluorobenzyl and 2-tetrahydrofurfuryl;

$R_a$ and $R_b$ represent, independently one from the other, a saturated or unsaturated alkyl containing from 1 to 4 carbon atoms or they may form, together with the nitrogen atom to which they are bound, a heterocyclic ring having 5 or 6 members, such as, for example, the pyrrolidine or piperidine group.

A further object of the invention is formed by the non-toxic addition salts of the compounds of formula (I) with suitable pharmaceutically acceptable acids. In particular the poly-addition salts with the halogen acids, such as hydrochloric, hydrobromic and hydroiodic acid and, more particularly, the dichlorohydrate salts being preferred.

The compounds (I) are obtained by reaction of 2-methylbenzimidazoles of formula

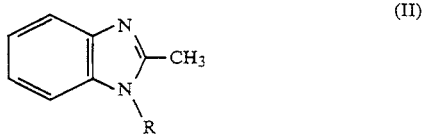

wherein R is as above specified, with formaldehyde, as such or in polymeric form, and with a suitable salt of a secondary amine of formula:

The reaction is carried out using two or more molar equivalents of formaldehyde and of the salt of the secondary amine (III) for molar equivalent of 2-methylbenzimidazole (II) in the presence of a suitable solvent selected between water or a straight or branched alcohol containing from 1 to 5 carbon atoms, or their suitable mixtures, at a temperature between room temperature and reflux temperature of the solution, for a period of time between 10 minutes and 12 hours.

The compounds (I) of the invention are preferably isolated as addition salts with halogen acids from which, by neutralization with a stoichiometrical quantity of aqueous diluted solutions of bases such as hydrates, bicarbonates and/or alkaline carbonates or alkaline-earth carbonates or with ammonia, the corresponding free bases may be obtained.

From the compounds (I), in the form of free bases, other addition salts with suitable pharmaceutically acceptable acids may be eventually obtained. The preferred reaction conditions are those which use from 2.3 to 2.4 molar equivalents of formaldehyde and amine salt (III). The amine salts of formula (III) are preferably represented by hydrochlorides and the preferred reaction solvents are constituted by the isopropyl, t-butyl, n-butyl and t-amyl alcohols. The reaction is preferably carried out in a period of time between 2 and 5 hours.

The starting 2-methylbenzimidazole derivatives (II) are prepared using a procedure well known in the art, such as for example, by reaction of 2-methylbenzimidazole with a halide Hal R, where Hal represents a chlorine, bromine and iodine atom, chlorine being the preferred one, and R has the above cited meaning, in the presence of bases, in an inert solvent. Suitable halides are represented by chlorides, bromides and iodides of ethoxyethyl, allyloxyethyl and tetrahydrofurfuryl, but the chlorides thereof and the benzylchloride and the 4-fluorobenzylchloride are already sufficiently reactive to complete the reaction. As bases carbonates, amides, hydrates and/or potassium and sodium alcoholates are used; the inert solvent is represented by a suitable ketone such as acetone, methylethylketone, by a linear or branched alcohol containing from 1 to 4 carbon atoms, from dimethylformamide, N-methylpyrrolidone, dimethylsulfoxide and their mixtures.

The 2-(benzimidazol-2-yl)-1,3-diaminopropane derivatives (I) have proved to possess an interesting anti-allergic activity; thus they are useful as anti-allergic agents and can be mixed with suitable carriers and suitably formulated in pharmaceutical compositions suitable for oral and parenteral administration. Oral administration is preferred.

For therapeutic administration, the compounds according to the present invention are used in the form of pharmaceutical preparations which contain said compounds in admixture with pharmaceutically acceptable carriers such as an organic or inorganic solid or liquid excipient suitable for oral or parenteral administration. The compounds of the invention may be contained in such pharmaceutical preparations in the form of a free base or in the form of their non-toxic acid addition salts. The inorganic acids which may be employed to prepare these acid addition salts may be, e.g., hydrochloric or sulphuric acid. The organic acids which may be employed are, e.g., maleic, fumaric and succinic acid.

The pharmaceutical preparations may be in solid form as capsules, tablets, dragees or in liquid form such as solutions, suspensions or emulsions. If desired, there may be included in the above preparations auxiliary substances such as stabilizing agent and other commonly used additives, or there may be contained other therapeutically active agents suitable to be administered together with the compounds of the invention. The dosage of the compounds will vary depending upon the route of administration route and will also depend upon the age and condition of the patient. Preferred dosages are, for example, from 0.1 mg/kg to 2 mg/kg and most preferably from 0.5 to 1 mg/kg.

The compounds of formula (I) are also useful as intermediates for the synthesis of 2-aminoethylbenzimidazole of formula

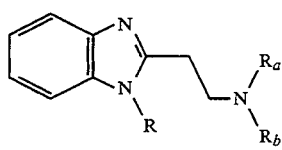

wherein R, $R_a$ and $R_b$ have the above described meanings. Said 2-aminoethylbenzimidazoles (IV) constitute an interesting class of anti-allergic compounds which belong to the class of compounds described in EP A-350 467 in the name of the applicant, which is herein incorporated by reference.

In fact, said compounds of formula (IV) are easily prepared by solvolysis of one of the aminomethylene residues which are present in the 2-(benzimidazol-2-yl)-1,3-diaminopropane derivatives of formula (I) after treatment with aqueous diluted mineral acids.

The following Examples are given by way of better illustrating the invention.

EXAMPLE 1

2[1-(2-Ethoxyethyl)benzimidazol-2-yl]-1,3-bis-dimethyl-aminopropane dichlorohydrate Grams 94 of potassium t-butylate are added, in portions, to a suspension formed by 100 g of 2-methylbenzimidazole in 250 ml of N-methyl-2-pyrrolidinone. The reaction mixture is heated to 90° C. under stirring for thirty minutes and to it 95 g of 2-chloroethylethylether are added in drops over a period of thirty minutes and then kept under stirring for a further hour. The reaction mixture is then cooled to room temperature and diluted with 200 ml of toluene, 450 ml of water and 100 ml of 35 % hydrochloric acid. When the phases are separated, the aqueous phase is extracted at pH 10 with 250 ml of toluene and the organic phase is first washed with 100 ml of water, then made anhydrous and concentrated under reduced pressure. The raw product obtained is distilled at 160°–165° C. (1 mmHg). Grams 127 of 1-ethoxyethyl-2-methylbenzimidazole are obtained.

Grams 21 of 1-ethoxyethyl-2-methylbenzimidazole are added, under stirring and in a single portion, to a suspension of 10 g of paraformaldehyde and 27 g of dimethylamine hydrochloride in 50 ml of t-butyl alcohol, heated to 70° C. The reaction mixture is heated to reflux for one and a half hours after which 26 g of crystalline 2-[1-(2-ethoxyethyl)benzimidazol-2-yl)]-1,3-bis-dimethylaminopropane dihydrochloride are obtained and isolated by filtration after cooling to room temperature; melting point 185°–189° C.

EXAMPLES 2–5

Operating in a similar way, as described above, are obtained:

Ex. 2) 2-[1-(2-allyloxyethyl)benzimidazol-2-yl)]-1,3-bis-dimethylaminopropane dihydrochloride.

Ex. 3) 2-(1-benzylbenzimidazol-2-yl)-1,3-bis-dimethylaminopropane dihydrochloride.

Ex. 4) 2-[1-(4-fluorobenzyl)benzimidazol-2-yl)]-1,3-bis-dimethylaminopropane dihydrochloride.

Ex. 5) 2-[1-tetrahydrofurfuryl-2-yl)benzimidazol-2-yl]-1,3-bis-dimethylaminopropane dihydrochloride.

EXAMPLE 6

1-Ethoxyethyl-2-[(2-dimethylamino)ethyl]benzimidazol dihydrochloride

A solution formed by 2.5 g of 2-[1-(2-ethoxyethyl)-benzimidazol-2-yl)]-1,3-bis-dimethylaminopropane dihydrochloride in 100 ml of aqueous 2N hydrochloric acid is heated under stirring for one hour to 90°–100° C. After cooling to room temperature, the reaction mixture is brought to pH 8.5 and extracted twice with 100 ml of toluene.

The organic phases are collected together and washed with 20 ml of water and acidified with 20 ml of 35% hydrochloric acid. The phases are separated, the aqueous phase is concentrated azeotropically with absolute ethyl alcohol until a crystalline solid is obtained, which is dissolved hot in 50 ml of absolute ethyl alcohol and, after dilution with 250 ml of acetone, is allowed to crystallize. Grams 12 of 1-ethoxyethyl-2-[(2-dimethylamino)ethyl]benzimidazol dihydrochloride melting at 158°–159° are obtained.

EXAMPLE 7

2-[1-(2-Ethoxyethyl)benzimidazol-2-yl)]-1,3-bis-dimethylaminopropane

To a solution of 3 g of 2-[1-(2-ethoxyethyl)-1-benzimidazol-2-yl)]-1,3-bis-dimethylaminopropane dihydrochloride in 10 ml of water is added, at 0°–15° C. and under stirring, a molar excess of a saturated solution of sodium bicarbonate. After the development of the carbon dioxide is over, the mixture is repeatedly extracted with ethyl ether (2×8, 1×4 ml). The organic phases are collected together, washed with 4 ml of a saturated solution of sodium chloride, made anhydrous on sodium sulphate and evaporated to dryness under vacuum to obtain 2.1 g of 2-[1-(2-ethoxyethyl)benzimidazol-2-yl)]-1,3-bis-dimethylaminopropane as an oil. IR (film): 3390 (broad), 2775, 2825, 2855, 2950, 2975, 1618, 1505 $cm^{-1}$.

EXAMPLE 8

2-[1-(2-Ethoxyethyl)benzimidazol-2-yl)]-1,3-bis-dimethyl-aminopropane trihydrochloride To a solution of 0.32 g of 2-[1-(2-ethoxyethyl)benzimidazol-2-yl)]-1,3-bis-dimethylaminopropane in 1 ml of absolute ethyl alcohol are added 2 ml of a solution of 3N hydrochloric acid in absolute ethyl alcohol. By further diluting with acetone, 0.38 g of 2-[1-(2-ethoxyethyl)benzimidazol-2-yl)]-1,3-bis-dimethylaminopropanetrihydrochloride melting at 159°–160° C. (with dec.) are obtained.

We claim:

1. Derivatives of 2-(benzimidazol-2-yl)-1,3-diaminopropane of the formula

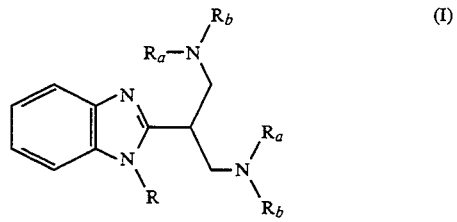

wherein:

R is selected from the group consisting of ethoxyethyl, allyloxyethyl, benzyl, 4-fluorobenzyl and 3-tetrahydrofurfuryl;

$R_a$ and $R_b$ represent, independently one from the other, a saturated or unsaturated alkyl containing from 1 to 4 carbon atoms or they may form, together with the nitrogen atom to which they are bound, a heterocyclic ring selected from the group formed by pyrrolidine and piperidine and their non-toxic pharmaceutically acceptable addition salts.

2. Derivatives of 2-(benzimidazol-2-yl)-1,3-diaminopropane according to claim 1, characterized by the fact that $R_a$ and $R_b$ represent, independently one from the other, a saturated or unsaturated alkyl containing from 1 to 4 carbon atoms.

3. 2-[1-Ethoxyethyl)benzimidazol-2-yl)]-1,3-bis-dimethylaminopropane dihydrochloride.

4. Pharmaceutical composition having anti-allergic activity characterized by containing an effective therapeutical quantity according to claim 1 in admixture with one or more suitable pharmaceutically acceptable carriers.

5. Pharmaceutical composition having anti-allergic activity characterized by containing an effective therapeutical quantity according to claim 2 in admixture with one or more suitable pharmaceutically acceptable carriers.

6. Pharmaceutical composition having anti-allergic activity characterized by containing an effective therapeutical quantity according to claim 3 in admixture with one or more suitable pharmaceutically acceptable carriers.

* * * * *

UNITED STATES PATENT AND TRADEMARK OFFICE
CERTIFICATE OF CORRECTION

PATENT NO. : 5,436,262
DATED : July 25, 1995
INVENTOR(S) : Marco MANTOVANINI ET AL It is certified that error appears in the above-indentified patent and that said Letters Patent is hereby corrected as shown below:

Column 4: Line 6, should read -- 2.6 g -- instead of "2.5 g".

Column 4: Line 40, should read -- 2865 -- instead of "2855".

Signed and Sealed this

Twelfth Day of December, 1995

Attest:

BRUCE LEHMAN

*Attesting Officer*  *Commissioner of Patents and Trademarks*